(12) United States Patent
Ribak

(10) Patent No.: US 8,851,671 B2
(45) Date of Patent: Oct. 7, 2014

(54) SYSTEM AND METHOD FOR FAST RETINAL IMAGING

(75) Inventor: Erez Ribak, Haifa (IL)

(73) Assignee: Technion Research and Development Foundation Ltd, Technion, Haifa (IL)

( * ) Notice: Subject to any disclaimer, the term of this patent is extended or adjusted under 35 U.S.C. 154(b) by 8 days.

(21) Appl. No.: 13/541,677

(22) Filed: Jul. 4, 2012

(65) Prior Publication Data

US 2013/0176531 A1    Jul. 11, 2013

Related U.S. Application Data

(62) Division of application No. 12/336,567, filed on Dec. 17, 2008, now Pat. No. 8,226,232.

(51) Int. Cl.

| | |
|---|---|
| *A61B 3/14* | (2006.01) |
| *A61B 3/12* | (2006.01) |
| *H04N 7/18* | (2006.01) |
| *G01B 11/22* | (2006.01) |
| *G01B 11/25* | (2006.01) |
| *G06T 7/00* | (2006.01) |
| *A61B 5/00* | (2006.01) |

(52) U.S. Cl.
CPC .. *H04N 7/18* (2013.01); *A61B 3/14* (2013.01); *A61B 3/12* (2013.01); *G01B 11/22* (2013.01); *G06T 2207/30041* (2013.01); *G01B 11/2513* (2013.01); *A61B 5/0073* (2013.01); *G06T 7/0057* (2013.01)
USPC ........................................ 351/206; 351/246

(58) Field of Classification Search
CPC ........ A61B 3/103; A61B 3/02; A61B 3/1015; A61B 3/14; A61B 3/12
USPC .................................. 351/200, 205–206, 246
See application file for complete search history.

(56) References Cited

U.S. PATENT DOCUMENTS

| | | | |
|---|---|---|---|
| 4,883,061 A | 11/1989 | Zeimer | |
| 5,220,360 A | 6/1993 | Verdooner et al. | |
| 5,303,709 A * | 4/1994 | Dreher et al. | 600/476 |

(Continued)

FOREIGN PATENT DOCUMENTS

| | | |
|---|---|---|
| CA | 2284299 | 3/2001 |
| WO | 2006/030413 | 3/2006 |

OTHER PUBLICATIONS

Milbocker et al., in Applied Optics, vol. 30, p. 4148 (1991).

(Continued)

*Primary Examiner* — James Greece
(74) *Attorney, Agent, or Firm* — Edward Langer

(57) ABSTRACT

An optical system and measurement method for imaging three-dimensional objects with low light scatter comprising at least one source of radiation; a radiation projection means for creating a set of foci through a volume of an object; and a means for imaging the returned light from the set of foci on at least one camera, wherein the imaging of the volume of the object is at a different angle from the projection, allowing for detection of the returned light on separate camera pixels. The measurement method further comprises projecting a longitudinal grid of elongated foci through the volume of an object; imaging returned light from the object at a different angle on at least one camera, so as to avoid overlapping the elongated images; and analyzing the imaged, returned light to yield depth information of the object at a multiplicity of points.

7 Claims, 2 Drawing Sheets

(56) References Cited

U.S. PATENT DOCUMENTS

| | | | |
|---|---|---|---|
| 5,993,001 A * | 11/1999 | Bursell et al. | 351/212 |
| 6,267,477 B1 | 7/2001 | Karpol et al. | |
| 6,276,799 B1 * | 8/2001 | Van Saarloos et al. | 351/206 |
| 2008/0284981 A1 * | 11/2008 | Fercher | 351/221 |

OTHER PUBLICATIONS

Wanek et al., "Effect of aberrations and scatter on image resolution assessed by adaptive optics retinal section imaging", Journal of the Optical Society of America A, vol. 24, p. 1295-1304 (2007).

Ribak et al., Proceedings of the European Southern Observatory, vol. 58, p. 281 (2001).

Slit Lamps, by Haag-Streit, Cat. No. BQ 900, Mason, Ohio, USA.

Prati et al., "Expert review document on methodology, terminology, and clinical applications of optical coherence tomography . . . ", European Heart Journal, Nov. 4, 2009.

Bellmann et al., "Fundus autofluorescence imaging compared with different confocal scanning laser ophthalmoscopes", Br J Ophthalmol 2003; vol. 87: p. 1381-1386 doi:10.1136/bjo.87.11.1381.

* cited by examiner

SYSTEM AND METHOD FOR FAST RETINAL IMAGING

CROSS-REFERENCE TO RELATED APPLICATION

The present application is a Divisional of U.S. parent patent application Ser. No. 12/336,567 filed Dec. 17, 2008 by the Applicant, the contents of which are hereby incorporated by reference.

FIELD OF THE INVENTION

The present invention generally relates to the field of imaging three-dimensional objects with low light scatter, and more particularly, to a system and method for fast retinal imaging by parallel projections and extraction of parameters from such retinal images.

BACKGROUND OF THE INVENTION

One of the main difficulties today in ophthalmology is the lack of a good tomographic device which will give an instant picture of large parts of the retina and provide depth information at the same time. There are cameras which scan through the retina and there are cameras which take one or more images. Thus the choice of the ophthalmologist is between having good depth information in a few and sometimes unknown locations or a superficial picture of larger areas of the retina, but without depth information.

Such information is necessary in order to prevent some of the most blinding diseases, if only detected early enough. The prevalence of retinal diseases is significant among the older population, and early discovery of these diseases allows treating them in time, thus preventing full blindness of the patients. This early discovery is difficult because of a few reasons. Firstly, the optics of the eye hinder detection of details smaller than ten microns across, and usually even much coarser details are not seen. While adaptive optics, in the future, might partially solve this problem, it is still limited by technology and by availability.

Even if the optics problems are solved, one still has to measure the retina in depth, somewhat as in microscopy. This means getting three-dimensional pictures of the retina.

Prior art instruments which provide three-dimensional images of the retina are well-known by those skilled in the art. Current and commercially available devices are slit lamps, Optical Coherence Tomography (OCT) devices and confocal Scanning Laser Ophthalmoscopes (cSLO). They are all described in medical and optical literature.

Unfortunately different schemes to get these depth pictures require some kind of scanning, which leads to other problems. As the area and depth are divided into more resolution elements, it becomes nearly impossible to accumulate them all in a single picture. Simple slit lamp scanning, OCT, and cSLO (confocal microscopy) go sequentially from one point in the retina to the next, which must take time. Unfortunately, the patient's eye is a live object and it moves during scanning.

In the slit lamp, for example, a sheet of light illuminates a curve across the retina, and a camera is used for looking from the side, measuring the shape and intensity of the imaged light. The process is sequentially repeated by illuminating one slice after another of the retina. The major drawback is the fact that the eye frequently moves between these scans. This means that the separate scan results may no longer be ordered in space as they were intended, and special efforts must be taken to fit them into their original locations and to produce a composite full image.

In Optical Coherence Tomography (OCT), there is also a three dimensional scan, in two lateral directions and in depth. In newer versions some of these scans are replaced by direct imaging of the whole surface or by Fourier scanning. In OCT depth resolution is the best, but the scanning is slow. As a result, the emerging picture is not continuous. For cases where following the disease over time is essential, it is sometimes next to impossible to scan the same region again.

In confocal microscopy—i.e., using confocal Scanning Laser Ophthalmoscopes (cSLO)—a single beam is focused at a location in the retina, and the reflected image is scanned in depth through a pin-hole simultaneous with the beam, providing depth information at this point. The process is repeated at the next spot of light, and again it is hoped that the eye does not move between these scans. In some applications, multiple foci are provided simultaneously, and scattered light is imaged through a corresponding array of pinholes.

U.S. Pat. No. 4,883,061 to Zeimer, and U.S. Pat. No. 6,267,477 to Karpol and Zeimer disclose imaging scanning apparatuses and methods for retinal thickness non-invasive analysis. They include a light source, separate or common focusing optic and beam deflector for incident and reflected beams going to and returning from the retina of an eye, and an imaging device. The apparatus further includes separate optical paths for imaging the fundus and iris of the eye. An eye model is obtained by spatially integrating images of the retina, the fundus and the iris.

Specifically, Karpol and Zeimer in U.S. Pat. No. 6,267,477 teach using a single scanning laser beam for measuring retinal thickness while " . . . changing the beam profile so that the subsequent profile of the beam at the retina is slit shaped and not dot shaped."

To parallelize the scan, Basu and Moore, in Canadian Application CIPO 2284299, scan an array of lines or dots across the retina, or alternatively let the eye scan across such an array, and combine their results into a three-dimensional map of the retina. Similarly, Verdooner et al. in U.S. Pat. No. 5,220,360, rotate a grid of parallel lines to fall on the retina at cross directions. The different line images are narrowed or skeletonized in software, as is known to those skilled in the art, to create a retinal topographic map, essentially assuming a single surface reflection.

Why is retinal slit scan preferred? Milbocker and Reznichenko, in *Applied Optics*, Vol. 30, p. 4148 (1991), prove mathematically and experimentally that having the beam arrive from one side of the pupil, and depart from the opposite side, has the best depth resolution. This resolution is more than double compared to methods where the beams arrive from the side and leave from the pupil center, or the other way round.

In the *Journal of the Optical Society of America A*, vol. 24, p. 1295 (2007), Wanek, Mori and Shahidi say about a system equivalent to that of Karpol and Zeimer: "We have developed an optical section retinal imaging technique with high spatial resolution and a depth resolution intermediate between that of SLO and OCT. Though our technique has lower depth resolution than OCT, it offers the advantages of higher image acquisition rate, better coverage for retinal thickness mapping, and flexibility in varying the incident laser wavelength to image fluorescence as well as reflectance." Nevertheless, this is still a scanning technique.

The limitation of all scanning methods is that later data processing tries to remove the discontinuities in the scanned volumes. This is important also if one wishes to identify and track retinal positions for later follow-ups. All of these problems are much easier if the whole retina is measured in one take, without the need for repetitive scans and measurements. In this case, there is no ocular movement, no need to stitch the scans back together into the image, and no attendant distortion in the result.

In WIPO application WO2006/030413 to Iddan et al. a large area of the retina is illuminated, being imaged through a Hartmann-Shack wave front sensor. This is performed without scanning. However, since the light source (namely the retina) in this prior art device is extended, the sensor fails to provide directional information about the returned beam.

The example of the retina is brought because of the many constraints encountered in both illumination and detection through the pupil, in the presence of aberrations which distort both incoming and outgoing beams. There are different, usually easier, constraints in other applications such as visualizing the depth information of nearly-transparent objects, such as plastics, gels, smoke or steam, biological in-vivo and in-vitro samples and more. If there is some light scattered within these objects, it can be used to trace their internal structure in three dimensions. In other cases, fluorescence is used, then again in others non-linear effects, one or more of these mechanisms serving to illuminate the light path when observed in directions other than the original one. Here, and hereinafter, these different mechanisms and processes are referred to in the general name of scattering, without losing generality.

In microscopy and other applications, one uses structured light: a scanned sheet of light, or a set of such sheets, which illuminate the sample. Light scattered from the sample along these sheets is then detected in a different aspect angle. Deviations and intensity variations in the scattered image of the sheet are translated into positional information and scatterer density. Stroboscopic methods allow separation of the sheets in time and thus in space. If the sheets are all illuminated at the same time, they must be separated such that the light returned from each of them does not become mixed-up with light scattered from others. This is the "venetian blind effect", described by Ribak and Ragazzoni in the *Proceedings of the European Southern Observatory*, vol. 58, p. 281 (2001). The venetian blind effect imposes strict limitations on the mutual spacing of the sheets or on separate light beams, in the sense that the light scattered from separate sheets or foci does not fall on the same detector pixel.

In some of the prior art applications the time factor is important, such as in those involving smoke or steam turbulent motion, and scanning the structured light is too slow. In some other examples one wishes to avoid moving components and successive illumination of the light sheets or foci, and in others, speed of measurement is important. So concentrating on the more limiting example of retinal imaging does not limit the present invention only to this example; rather it serves as a descriptive means.

Thus there is a need for a system and a method to enable capturing a single-shot picture of a three-dimensional object, such as the retina of the eye or a non-ocular object, taken during a time when the object is immobile to provide depth information about the object.

SUMMARY OF THE INVENTION

Accordingly, it is a broad object of the present invention to overcome the above disadvantages and limitations of the prior art by providing a system and a method for enabling taking a single picture of a three-dimensional object, such as the retina of the eye, the picture being captured at such a speed that the object does not move or change during the picture acquisition, thus facilitating construction of depth information about the retina or object.

Another object of the present invention is to provide an optical system used to create a set of foci projected throughout a volume of an object and to image the scattered light from the set of foci on at least one camera.

Yet another object of the present invention is to provide a method for imaging of the object at a different angle from the projection direction, so as to allow detection of scattered light from different depths on different camera pixels.

Consider a camera with, for example, four thousand picture elements (pixels) across. It may be required that the retina is to be measured in, for example, five milliseconds, when the eye is assumed stationary. If the pixel spatial resolution is, for example, twenty-five micrometers when projected on the retina, then the measured field of view will be 0.025 times 4000, or 100 millimeters across, much bigger than the whole retina.

If the resolution now includes also depth resolution, say fifty points in depth (the retinal thickness is nearly half a millimeter), then the field will drop to two millimeters (100 divided by 50) across. This field will now be composed of eighty by eighty by fifty volume resolution elements (voxels). Larger detectors and color-parallel detectors will allow large area coverage and color information extraction as well. Choice of different width, breadth, and depth voxels can also be made. Trade-off between resolution, area coverage and number of pixels in the camera may be made for optimizing the device for the application. To summarize, it is seen that a two-dimensional camera presented with depth information, taken in one shot, is sufficient for the purposes of the present invention in accordance with the principles thereof.

Thus there is provided an optical system comprising:
at least one source of radiation;
a means for projecting said at least one source of radiation and creating a set of foci through a volume of an object;
a means for imaging returned light from the set of foci on at least one camera,
wherein the imaged returned light on the at least one camera is captured at a different angle than the projection of the at least one source of radiation through the volume of said object, so as to allow detection of the returned light on separate camera pixels to produce immediate depth information defining three-dimensional characteristics of said object.

In a preferred embodiment of the present invention, the foci are parallel to each other when passing through the object.

In another embodiment, the foci arrive at different angles at the object.

In yet another embodiment, the foci are parallel to each other when passing through the object, and the depth information is variable between the foci.

In still another embodiment, the foci arrive at different angles at the object, and the angular information is variable between the foci.

In a further embodiment, the foci arrive tilted at the object, and the tilt allows better depth separation.

In another embodiment, the set of foci is projected on a tissue.

In yet another embodiment, the tissue comprises the eye or parts thereof, such as the retina, the cornea, and the crystalline lens of the eye.

In another preferred embodiment of the present invention, the object comprises transparent or semi-transparent matter.

In accordance with a preferred embodiment of the present invention, there is also provided a measurement method comprising the steps of:

provviding at least one source of radiation;

projecting a longitudinal grid of elongated foci on an object through its volume;

imaging returned light from the projected object at a different angle on at least one camera, so as to avoid overlapping the elongated images on the at least one camera; and analyzing the imaged, returned light to yield depth information of the object at a multiplicity of points.

The depth information may involve polarization and ellipsometric information. Alternatively, the analysis comprises combining the depth information from the at least one camera into a continuous volumetric image of the object. In another embodiment of the present invention the analysis comprises combining images of different volumes of the object to make one volumetric image.

It should be stressed that the application of multi-spot imaging to the retina of the eye is one of many such applications. As a similar example, transparent or semi-transparent layers of organic or inorganic matter can be measured in microscopy, in vivo, ex vivo and in other configurations. This depth measurement can also be applied to non-layered matter and to any nearly-transparent material.

One of the more interesting applications of the method of the present invention is for measurement of material during processing or for quality control. For example, if one wishes to measure the uniformity of a transparent protective layer (or layers) on top of some product, it is possible to not only measure the thickness of the layer, but also its constituents and how they change across the product.

Similarly, ellipsometric sampling allows measurement of the complex refractive index, single or multi-layered. Taking these measurements at different points in the sample allows their comparison. Moreover, by taking them at varying angles at equivalent or nearby positions, comparison between the spots improves the ellipsometric results. In what follows reference will be in general to retinal imaging, but the same technology can be applied to other organic or inorganic matter.

Other features and advantages of the present invention will become apparent from the following drawings and descriptions.

BRIEF DESCRIPTION OF THE DRAWINGS

For a better understanding of the present invention with regard to the embodiments thereof, reference is made to the accompanying drawings, not to scale, in which like numerals and letters designate corresponding elements or sections throughout. For clarity, non-essential elements are omitted from some of the drawings. These might include, for example, complex lenses and optical elements represented schematically by thin lenses or not shown, or electric and electronic wiring for the cameras or light sources and modulators.

In the drawings.

DETAILED DESCRIPTION OF EMBODIMENTS OF THE INVENTION

Figure 1:
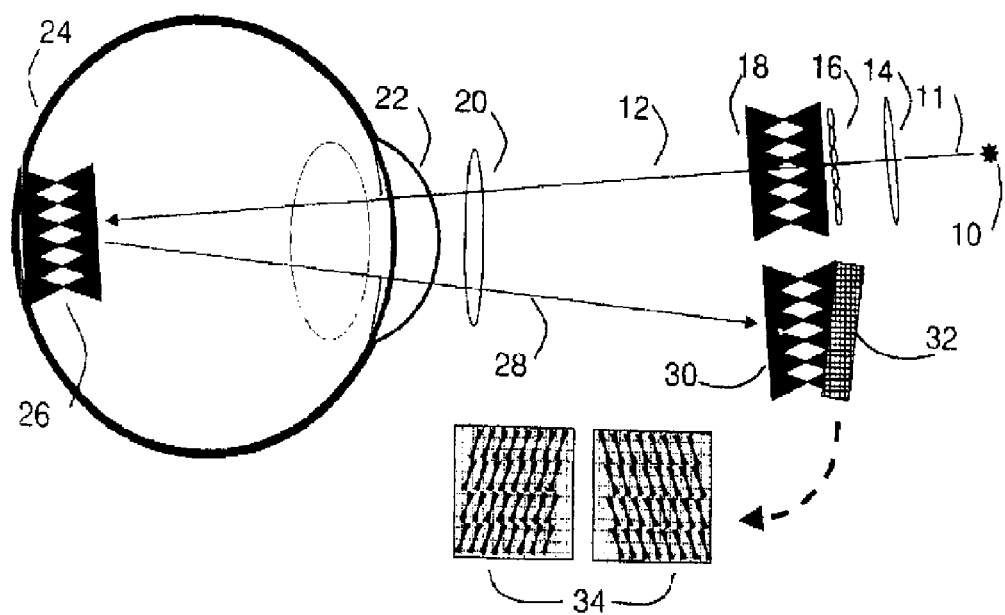
FIG. 1 is a schematic depicting an optical system for examining the eye, shown in cross-section, in accordance with a preferred embodiment of the present invention.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

It is to be understood that the invention is not limited in its application to the details of construction and the arrangement of the components set forth in the following description or illustrated in the drawings. The invention is capable of other embodiments or of being practiced or carried out in various ways.

Unless otherwise defined, all technical and scientific terms used herein have the same meaning as commonly understood by one of ordinary skill in the art to which the present invention belongs. In case of conflict, the present invention described and explained hereinbelow, together with the accompanying drawings and definitions, will control. It is to be understood that the phraseology and terminology employed herein is for the purpose of description and should not be regarded as limiting.

FIG. 1 is a schematic depicting an optical system for examining the eye, shown in cross-section, in accordance with a preferred embodiment of the present invention. The present invention provides a system and method to achieve parallel depth measurements of a transparent tissue, or layer, being imaged directly, under a microscope or at the eye (such as the retina, the cornea, or the crystalline lens).

A narrow band white light source 10, such as a laser source, projects a beam 11 through an optical system 14, including a lenset array 16 (or alternatively, an acoustic modulator, hologram or LCD), as is known to those skilled in the art. This produces foci arrays 18 which comprise a three-dimensional beam array, or two arrays in two colors projected thereafter as entry beams 12. Additional optics 20 are provided for forming an image 26 of foci array 18 on the retina of an eye 24, and to receive a reflected, return image 30 which is conveyed through the additional optics 20 by return beam 28 and directed at a slightly different angle from the retina of eye 24. This projection forms one or more return images 30 on one or more camera detectors 32.

A dashed arrow line draws attention to schematics 34 showing the appearance of a grid of foci formed from return images 30 on different camera detectors 32 at exit angles, each different from the entry angle and from each other in accordance with the principles of the present invention.

The method in accordance with the present invention comprises illuminating the tissue of eye 24 at an angle with a large number of narrow entry beams 12, separated in space from each other, similar to the arrangement of a bed of nails or the hairs of a brush. When applied to the retina of eye 24, entry beams 12 are projected through the semi-transparent elements 22, including the cornea, iris, humours, and lens, of eye 24.

A plurality of these beams 12 form images 26, which are now observed at another angle, and possibly at yet another observation angle simultaneously. These oblique viewing angles will allow tracing the return beams 28 as they cross the semi-transparent elements 22, and detect where there are variations in the optical properties of the retinal tissues of the eye 24, such as enhanced scattering or reflection, or change of polarization, or change of spectrum of the reflected or scattered light.

Preferably, a single light source 10 is used. The light may be one of: broad band light such as white light, for example incoherent light of a lamp; narrow band light produced for example by Light Emitting Diode (LED); or coherent light produced by a laser. The light is passed through an optical system 14 which creates multiple parallel beams out of it. The beams may be collimated or focused.

Figure 2:
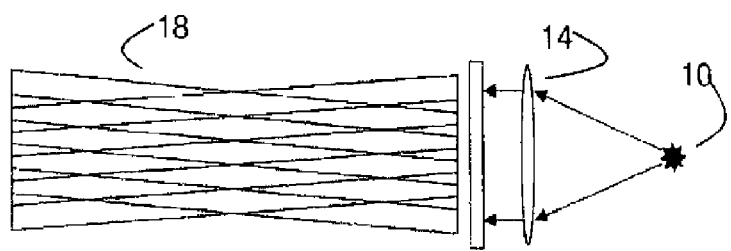
FIG. 2 schematically shows options to create an array of foci by a lenslet array, a hologram, or a liquid crystal device (LCD), in accordance with an exemplary embodiment of the invention.

FIG. 2 shows schematically options to create an array of foci by various means in accordance with an exemplary embodiment of the invention. For example, element 16 can be a grid of pinholes or a lenslet array. Such lenslet arrays are available on the market by a number of manufacturers, and they are usually made of glass or plastic, mostly for the purpose of wave front sensing. It is also a usual requirement that the density of lenslets is comparable to the wave front variations, and focal lengths thereof are short, so that the focal spots do not shift too much and do not overlap or even cross. Thus element 16 may be either fixed, or changed between images to have a different density or shape, as disclosed in U.S. Pat. No. 7,075,698 to E. N. Ribak, entitled "Variable Lenslet Array". In contrast to wave front sensing applications, in the present invention the requirement of short focal length can be relaxed.

Another way to achieve a plurality of beams is by providing a holographic device as depicted in FIG. 2. In a device like this, element 16 is a hologram incorporated in the optical path (indicated by parallel arrows) between the light source 10 and the target (not shown), creating a far-field pattern of sharp spots, such as can be found with some laser pointers. If necessary, hologram element 16 can be made at a higher density and also imprint polarization (such as linear or circular) on the multiple foci for ellipsometric or other measurements. In another option, element 16 can be a liquid crystal device (LCD) creating a mask or a hologram to form the set of foci.

In order to make the multiple foci narrower, element 16 of holograms or pupil masks can be added to make the beams with longer focal depth, or with oblique focus. Thaning, Jaroszewicz, and Friberg in *Applied Optics*, vol. 42, p. 9 (2003) describe masks or axicons allowing focal lines at oblique angles. The oblique focus line, when imaged from the other side of the pupil of an eye, is imaged onto a different number of pixels on a camera detector 32 (see FIG. 1), thus allowing better separation between the focus lines.

Optionally, instead of a single light source 10 it is possible to use a plurality of parallel radiation sources to create the multiple beams. As an example, an array of LEDs or quantum well lasers arrays form such a set of sources.

Reference is made again to FIG. 1. It is also possible to use two or more light sources and optical systems to create two or more comb arrays, with one or separate camera detectors 32 to measure each at yet different viewing angles. The multitude of beams is imaged onto the retina of the eye 24 through one or more sides of the pupil, again creating one or more two-dimensional foci arrays 26. The imaging camera detectors 32, or cameras, observe them from other sides of the pupil. Optionally, a plurality of light sources having different optical properties such as different wavelength or different polarization states can be employed.

In another embodiment of the present invention, instead of having one set of foci arrays and one or more cameras, there is provided one or more set of foci, and one camera which separates the images falling on it by wavelength or polarization or time. It should be noted that an independent continuous image is required to identify the location of a set of foci and variations thereof.

The light beams 12 are projected into the eye 24 using a part of the cornea and a part of the pupil, optionally with as little shared area with the outgoing beams 28. In terms of angular separation, the light scattered from the illuminating paths in the retina is now imaged at an angle different from the entry angle. This serves two purposes: to avoid direct reflections from the cornea or top surface of the tissue in order not to blind the camera detector 32, and to allow at the same time an oblique viewing of the rays or foci propagation in the retina. This side viewing separates the image of each ray or focus into many detector pixels, identifying each pixel with a different depth inside the retina.

During the measurement, the pupil may be dilated as known in the art. Dilation may provide larger angular separation between viewing angles, and hence better depth resolution. If artificial dilation is not employed, the pupil may dilate naturally in the dark and the result will be a single-shot exposure taken in this dilated state. In non-ocular applications, the angular separation between incoming 12 and outgoing 28 beams is less restricted.

A camera detector 32 (or each of a plurality of cameras) now has multiple images of the same scattering volume of rays or focal lines forming a foci array. If the rays have a clear focus in each one of them, these foci come originally from the same depth in the source, and hence from the same depth in the retina and in the final image. This allows a common depth surface to be established, something that is not quite easy with sequential scanners and with slit lamps as in the prior art. In accordance with the method of the present invention, an analysis consists of combining the depth information from camera detector 32 (or each of a plurality of cameras) into a continuous volumetric image of an object. Alternatively, an analysis consists of combining images of different volumes of the object into one volumetric image.

The quality of this depth surface depends on the quality of the optics, including that of the eye 24. It might be necessary to use adaptive optics, contact lenses or immersion goggles as disclosed for example in PCT Application WO06001013A2 to Ribak entitled "Goggles for improved ocular vision", to improve the image quality into and out of the most aberrated eyes. With or without adaptive or passive annulment of aberrations, illumination and observation occur through minimal areas of the pupil, as distant as possible from each other, to enhance depth resolution.

In accordance with another embodiment of the present invention, the system is integrated or added to an ophthalmic system such as a slit-lamp or a fundus camera (not shown) or other systems with scanning capabilities.

In yet another embodiment, using the system of the present invention, a few images are taken of parts of the retina in order to cover the entire retina, and then "stitched" together in software in a manner as is known to those skilled in the art.

In still another embodiment, a few images are taken of the same or overlapping areas of the retina, and parameters, for example retinal thickness, are extracted from overlapping areas of the images which are used to increase the Signal-to-Noise Ratio (SNR) of the parameters by registering and averaging these images.

Figure 3:
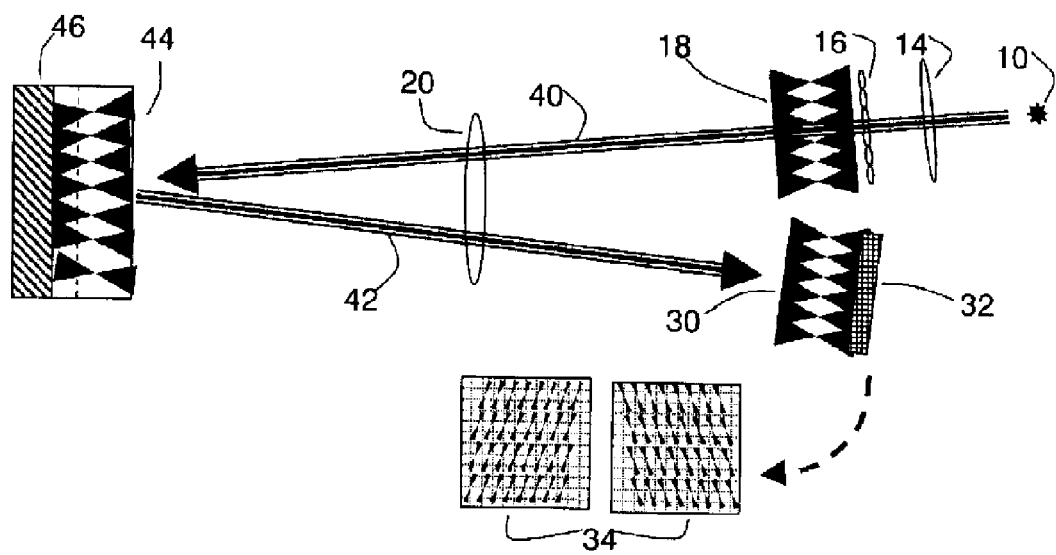
FIG. 3 is a schematic depicting an optical system for measuring non-ocular structures in accordance with another exemplary embodiment of the invention.

FIG. 3 is a schematic depicting an optical system for measuring non-ocular structures in accordance with another exemplary embodiment of the invention.

A light source 10 projects a beam through an optical system 14, as is known to those skilled in the art. A lenset array or other element 16 is provided which forms a two-dimensional foci array 18 which is projected as beam 40. Additional optics 20 are provided for imposing a projected image 44 of foci array 18 on the layered surface of a typical structure 46 which is generally flat. In this case one may want to acquire information about two kinds of problems, lateral inhomogeneity in the layers, and depth information for homogeneous layers. There are two options, either to send an array of parallel beams or foci, or to send an array of converging beams or foci.

In the first case of equal parallel beams, each returned beam 42 will be slightly different from the previous ones, as it has hit a position in a layer with a different thickness or other depth information. The location of the focus of a return image 30, as seen from the side by at least two cameras 32, will be different accordingly. A dashed arrow line draws attention to schematics 34 showing the appearance of a grid formed from return images 30 on different camera detectors 32 at exit angles, each different from the entry angle in accordance with the principles of the present invention.

In the second case, the difference between the entry beams 40 results from their hitting the same layers at different angles. This leads to different reflection profiles and to different polarization and spectral effects as a function of hitting and measurement angles. By measuring the intensities or polarizations of the return beams 42, it is possible to infer the layers profiles and complex refractive indices.

As a non-binding example, one of the methods to assess the material properties is ellipsometry, where the polarization of return beam 42 changes upon reflection from the sample structure 46. By measuring the Stokes parameters for each such reflected return beam 42, the variation between them will lead to different Stokes values. As each focal spot hits at a different angle and is being measured at a different angle, it yields ellipsometric data unique to these angles. The next focal spot will hit at a different angle and will add more data to the previous one, and so on. Polarizing and analyzing optics can be common to all return beams 42, or different for individual return beams 42, thus trading spatial resolution for polarization information.

The main advantage of this application is that by observing the focal lines or return beams 42 obliquely, these samples are measured also in depth, whereas previously all measurements assumed a single surface being measured. As a result, a camera detector 32 can take an image of the scattered light along each beam path and yield information along the beams, not only where they hit some surface.

Figure 4:
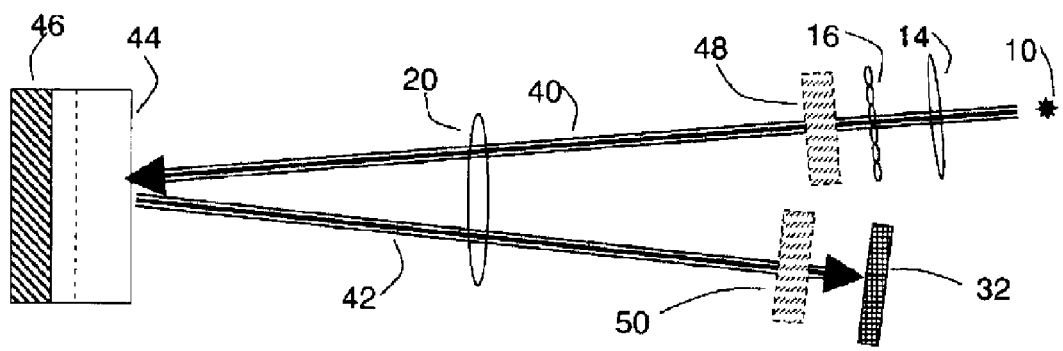
FIG. 4 schematically depicts still another exemplary embodiment of the present invention using optional, beam-modifying elements.

FIG. 4 schematically depicts still another exemplary embodiment of the present invention using optional, beam-modifying elements which are inserted in the beam path. The beam-modifying elements 48 and 50 may be inserted into the path of entry beam 40, the path of reflected return beam 42, or both.

For example, a beam-modifying element 50, such as a polarizer or analyzer, is used in front of camera detector 32 to perform polarization analysis of an image conveyed by rays 42 from structure 46 having semi-transparent layers 44. When the light source 10 is a laser, the entry beam 40 may be polarized due to the nature of the laser.

Alternatively, a polarizer beam-modifying element 48 may be inserted in the path of entry beam 40. The polarizer may be a fixed or rotating linear polarizer or circular polarizer, a wave-plate, mechanical or electronic, or a combination of these elements.

In another embodiment of the present invention, a liquid crystal device (LCD) (not shown) is used as polarization or retardation modification device. Optionally, the LCD is electronically controlled to dynamically change its properties during data acquisition.

In yet another embodiment, the light source 10 is a broad wavelength source such as a lamp, and the beam-modifying element 48 or 50 is a narrow band spectral filter or a monochromator.

In still another embodiment, an LCD is used as a spectral filter. Optionally, the LCD is electronically controlled to dynamically change its properties during data acquisition.

In yet a further embodiment, at least one beam-modifying element 48 or 50 is divided into pixels, so that at least two pixels have different optical properties. For example, a spectral filters array—such as a Red, Green and Blue (RGB) filters array—may be used to generate foci which are composed of different colors. Similarly, an array of polarizers may be used. The embodiment of the present invention utilizing an LC element may also be divided into pixels, for example, using an LCD.

Having described the present invention with regard to certain specific embodiments thereof, it is to be understood that the description and accompanying drawings are not meant as a limitation, since further modifications may now suggest themselves to those skilled in the art, and it is intended to cover such modifications as fall within the scope of the claims of the described invention.

I claim:

1. A measurement method comprising the steps of:
projecting, using at least one radiation source, a plurality of parallel, narrow entering light beams distinct in space onto an object, thereby generating a longitudinal grid of elongated foci on said object through its volume;
imaging returned light from said object at a different angle than an entry angle of said narrow entering light beams on at least one camera, so as to avoid overlapping and interfering with said elongated foci formed on said at least one camera; and
analyzing said imaged, returned light to yield depth information of said object at a multiplicity of points,
wherein said analysis yields polarization and ellipsometric information of said object at said multiplicity of points.

2. The method of claim 1, wherein said object is the retina of the eye, and illumination and detection are at opposite sides of the pupil.

3. The method of claim 1, wherein said analysis consists of combining said depth information from said at least one camera into a continuous volumetric image of said object.

4. The method of claim 1, wherein said analysis consists of combining images of different volumes of said object into one, more-extended volumetric image.

5. The method of claim 1, wherein said light illumination and detection are spatially multiplexed at a multiplicity of discrete wave lengths.

6. The method of claim 1, wherein said light illumination and detection are temporally multiplexed at a multiplicity of discrete wave lengths.

7. An optical measurement and examination method for examining and measuring the thickness of one of a transparent and nearly-transparent object, said method comprising:

projecting, from at least one source of radiation, a plurality of parallel, narrow entry beams substantially at one angle onto said object, thereby creating a set of foci through a volume of said object;

imaging scattered light returned at a different angle than said one angle of said entry beams on at least one camera, while avoiding overlapping and interference of images of said set of entry beams, analyzing said imaged, returned light to yield depth information of said object at a multiplicity of points, thereby allowing detection of said scattered light returning from different depths on separate camera pixels to produce three-dimensional volume characteristics of said object, wherein said analysis yields polarization and ellipsometric information of said object at said multiplicity of points.

* * * * *